United States Patent
Grundei

(10) Patent No.: US 6,843,808 B2
(45) Date of Patent: Jan. 18, 2005

(54) SUBCUTANEOUS, INTRA-MUSCULAR COUPLING FOR A RIGID TRANSCUTANEOUS IMPLANT

(75) Inventor: Hans Grundei, Lubeck (DE)

(73) Assignee: Eska Implants GmbH & Co. (DE)

( * ) Notice: Subject to any disclaimer, the term of this patent is extended or adjusted under 35 U.S.C. 154(b) by 1 day.

(21) Appl. No.: 10/332,736
(22) PCT Filed: May 18, 2001
(86) PCT No.: PCT/EP01/05726
§ 371 (c)(1), (2), (4) Date: Jan. 10, 2003
(87) PCT Pub. No.: WO02/13729
PCT Pub. Date: Feb. 21, 2002

(65) Prior Publication Data
US 2003/0109878 A1 Jun. 12, 2003

(30) Foreign Application Priority Data
Aug. 15, 2000 (DE) .......................... 100 40 590

(51) Int. Cl.⁷ .................................................. A61F 2/60
(52) U.S. Cl. ..................................................... 623/32
(58) Field of Search .............................. 623/27–32, 38, 623/53

(56) References Cited

U.S. PATENT DOCUMENTS

| | | | |
|---|---|---|---|
| 3,683,421 A | | 8/1972 | Martinie |
| 3,947,897 A | * | 4/1976 | Owens ..................... 623/11.11 |
| 4,143,426 A | * | 3/1979 | Hall et al. ..................... 623/53 |
| 4,158,895 A | * | 6/1979 | Frosch et al. ................. 606/60 |
| 5,002,578 A | * | 3/1991 | Luman .................... 623/22.42 |
| 5,041,137 A | * | 8/1991 | Nemoshkalov ............. 128/898 |
| 5,759,206 A | * | 6/1998 | Bassett ......................... 623/27 |
| 6,425,925 B1 | * | 7/2002 | Grundei ....................... 623/32 |
| 6,482,238 B1 | * | 11/2002 | Grundei ....................... 623/32 |
| 6,485,522 B1 | * | 11/2002 | Grundei ....................... 623/38 |

FOREIGN PATENT DOCUMENTS

| | | |
|---|---|---|
| DE | 43 38 746 | 5/1995 |
| DE | 198 26 638 | 12/1999 |
| DE | 198 57 907 | 4/2000 |
| DE | 199 31 882 | 5/2001 |
| FR | 2 787 018 | 6/2000 |
| SU | 1375254 | 2/1988 |

OTHER PUBLICATIONS

International Search Report.

* cited by examiner

Primary Examiner—Alvin Stewart
(74) Attorney, Agent, or Firm—Cantor Colburn LLP

(57) ABSTRACT

A subcutaneous, intramuscular bearing for a rigid transcutaneous implant that can be anchored intracorporeally in a bone stump and that has an extracorporeal coupling device for a standard exoprosthetic component that includes a flexible material, and that has a socket that distally surrounds the implant in a firm manner, the bearing including: an enveloping sheath arranged intracorporeally in the form of a flexible pleated bellows, which is proximally connected to the socket via a collar that is formed thereon in a sealing manner, in such a way that a hollow space with a minimum breadth s remains free between the inner walling of the pleated bellows and the outer walling of the socket; a flexible grid network is arranged distally at the pleated bellows; and an additional grid network adjoins the flexible grid network on the distal side, wherein the additional grid network has a higher modulus of elasticity in comparison to that of the flexible grid network.

6 Claims, 1 Drawing Sheet

SUBCUTANEOUS, INTRA-MUSCULAR COUPLING FOR A RIGID TRANSCUTANEOUS IMPLANT

SPECIFICATION

1. Field of the Invention

The present invention pertains to a subcutaneous, intra-muscular bearing for a rigid transcutaneous implant that can be anchored intracorporeally in a bone stump, and that has an extracorporeal coupling device for a standard exoprosthetic component.

2. Description of the Related Art

Such an implant for providing care to a patient who has undergone a thigh amputation has been described comprehensively in e.g., DE-198 26 638. According to this, an implant in the form of an adapter with a stem component is positioned in the intramedullary in the amputated femur stump. An intermediate piece adjoins the stem component, and exits through the point of emergence in the thigh stump. A problematic feature in this connection is the sealing off of the stump of the extremity because the opening location has to be kept aseptic. In addition, the adaptation of the rigid intermediate piece to the muscular surroundings within the thigh stump and to the skin is a critical point. Ideally, the skin, the muscle tissue, and the connective tissue must be capable of movement relative to the rigid implant. Of course, this requirement hampers efforts to keep the point of emergence aseptic.

A subcutaneous, intramuscular bearing of the type that was mentioned at the beginning is known from U.S. Pat. No. 4,158,895 and comprises a flexible material and it has a socket that distally surrounds the implant in a firm manner. In the case of this bearing, there is no mobility, relative to the rigid implant, of the soft tissues that surround the bearing.

A further important aspect is that a subcutaneous bearing must form an effective barrier against infection by germs from the outside.

Against this backdrop, the problem for the present invention is the further development of the subcutaneous bearing of this generic type so that the soft tissues are capable of moving relative to the rigid implant without the opening site in the stump part of the body being exposed to an increased risk of inflammation.

This problem is solved by the subcutaneous, intramuscular bearing with the characterizing features of claim 1. Advantageous further developments arise from the subsidiary claims.

SUMMARY OF THE INVENTION

A subcutaneous, intramuscular bearing including an enveloping sheath arranged intracorporeally in the form of a flexible pleated bellows, which is proximally connected to the socket via a collar that is formed thereon in a sealing manner, in such a way that a hollow space with a minimum breadth s remains free between the inner walling of the pleated bellows and the outer walling of the socket; a flexible grid network is arranged distally at the pleated bellows; and an additional grid network adjoins the flexible grid network on the distal side, wherein the additional grid network has a higher modulus of elasticity in comparison to that of the flexible grid network.

The socket is firmly seated on the implant component in question and is, for example, homogeneously glued to it in such a way that this seating of the socket on the implant component is germ-resistant. In this region, the enveloping sheath is shaped in the form of pleated bellows that can be manufactured from e.g., a silicone in the form of a single component that also includes the socket.

The configuration of the enveloping sheath in the form of a pleated bellows offers very good mobility of the soft tissues, which surround the bearing, relative to the rigid implant.

The aforementioned flexible grid network is positioned distally relative to the pleated bellows, which can also preferably comprise a silicone, and it is optionally configured in the form of a single component that also includes the pleated bellows. Together with the time period following the implantation, this flexible grid network ensures intimate bonding with the surrounding muscles.

The aforementioned additional grid network distally adjoins the flexible grid network, whereby this additional grid network is especially preferably manufactured from a metallic woven or matted wool comprising titanium. This titanium wool hereby enters into intimate bonding with the patient's skin in the bodily stump, i.e., the skin grows into the titanium netting.

The entire bearing is embedded in the bodily stump. Only the rigid implant emerges from the socket of the bearing and exhibits the aforementioned coupling device there for a standard exoprosthetic component.

Germs or particles of dirt cannot penetrate up to the bodily stump, but are caught in the hollow space of the bearing that is formed by the pleated bellows.

Using the configuration of the subcutaneous, intramuscular bearing in accordance with the invention, it is possible to provide a patient with an implant in his bone stump on a long-term basis without the fear of severe complications because of sepsis. Because of the ingrowth of skin into the titanium netting, and because of the ingrowth of muscle tissue into the silicone grid network, an exceedingly effective natural barrier is built up against the penetration of germs, etc., into the bodily stump.

BRIEF DESCRIPTION OF THE DRAWINGS

The invention will be explained in greater detail on the basis of an example of an embodiment in accordance with FIG. 1.

DETAILED DESCRIPTION

Figure 1:
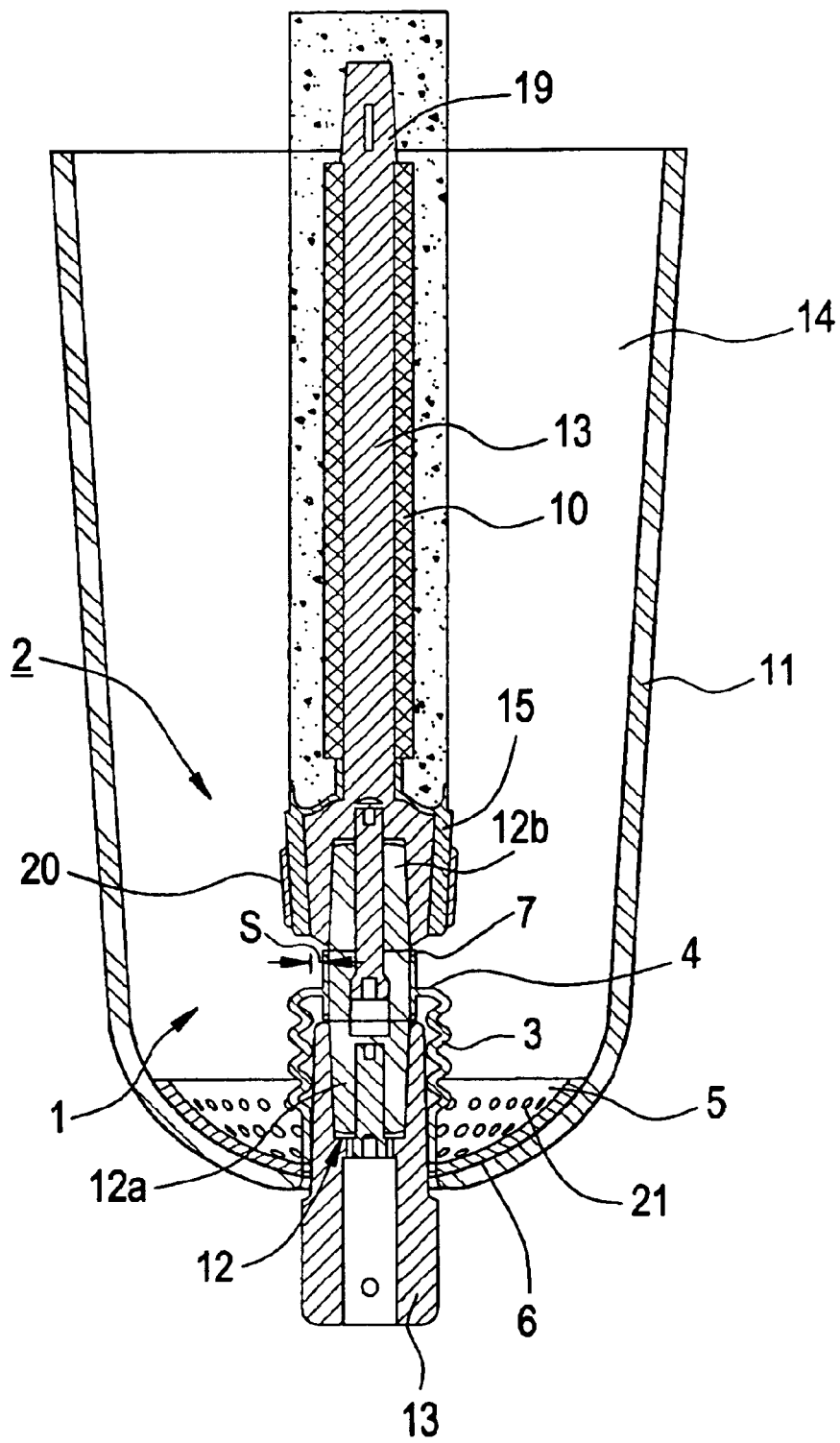

A thigh stump 14 is illustrated therein with the femur stump 10. A stem component 13 of the implant 2 is introduced into the tubular femur stump 10. An enveloping adapter 15 adjoins the 13 on the distal side, and encloses an intermediate piece 12 in the form of a double cone 12a and 12b. This intermediate piece is the connecting piece between the interior of the thigh stump and the extracorporeal surroundings. Accordingly, it passes through the skin 11 of the thigh stump 14. An extracorporeal coupling device 18 adjoins the section thereof that will be located on the outside, whereby this extracorporeal coupling device serves for accommodating a standard exoprosthetic component (not illustrated).

The bearing 1, which is arranged completely intracorporeally, i.e., subcutaneously and intramuscularly in the thigh stump 14, essentially comprises an inner tube or socket 7, which is cylindrical here and which is connected firmly to the implant 2 and, in the present case, is homogeneously glued to the intermediate piece 12 at the cylindrical transition region thereof. The gluing site forms a germ-resistant barrier to germs and dirt. The enveloping sheath 3 is arranged, in the form of a pleated bellows, over a collar 4 that is formed on the socket 7. The minimum breadth s between the outer walling of the socket 7 and the inner walling of the enveloping sheath 3 amounts to at least 1 mm, and can amount to up to 10 mm, for example.

On the distal side, the enveloping sheath 3 passes over, in the form of one piece of material, into a flexible grid network 5 with a large number of openings 21 that are penetrated by muscular tissue during the course of time following the operation.

On the distal side, an additional grid network 6 adjoins the grid network 5, whereby this additional grid network has a higher modulus of elasticity and, in particular, preferably consists of metallic wool that comprises titanium fibers. Skin tissue grows through this grid network 6 during the course of time following the operation.

The enveloping sheath 3, moreover, is provided at its periphery with an open mesh, three-dimensional, spatial netting structure 20 into which bone particles grow and, in this way, it forms an additional barrier against the penetration of germs on the osseous side.

The stem 13 of the implant 2, moreover, carries a similar surface in the interior of the bone canal.

At this juncture, mention might also be made of the proximal end 19 of the stem 13 that is configured here in the form of a plug-in cone and can serve as an adapter for a stem for an artificial hip joint.

What is claimed is:

1. Subcutaneous, intramuscular bearing for a rigid transcutaneous implant that can be anchored intracorporeally in a bone stump and that has an extracorporeal coupling device for a standard exoprosthetic component that includes a flexible material, and that has a socket that distally surrounds the implant in a firm manner, the bearing comprising:

an enveloping sheath arranged intracorporeally in the form of a flexible pleated bellows, which is proximally connected to the socket via a collar that is formed thereon in a sealing manner, in such a way that a hollow space with a minimum breadth s remains free between an inner walling of the pleated bellows and an outer walling of the socket;

a flexible grid network is arranged distally at the pleated bellows; and an additional grid network adjoins the flexible grid network on the distal side, wherein the additional grid network has a higher modulus of elasticity in comparison to that of the flexible grid network.

2. Bearing in accordance with claim 1, wherein the minimum breadth s amounts to 1 mm.

3. Bearing in accordance with claim 1, further comprising a silicone.

4. Bearing in accordance with claim 1, wherein the flexible grid network comprises a silicone.

5. Bearing in accordance with claim 1, wherein the additional grid network comprises a metallic woven or matted wool.

6. Bearing in accordance with claim 5, wherein the metallic wool is formed from titanium fibers.

* * * * *